United States Patent [19]
Daikuzono

[11] Patent Number: 5,190,535
[45] Date of Patent: Mar. 2, 1993

[54] LASER LIGHT TRANSMITTING PROBE

[75] Inventor: Norio Daikuzono, Chiba, Japan

[73] Assignee: S.L.T. Japan Company, Ltd., Tokyo, Japan

[21] Appl. No.: 543,313

[22] Filed: Jun. 26, 1990

[30] Foreign Application Priority Data

Jun. 30, 1989 [JP] Japan .................................. 1-169029

[51] Int. Cl.$^5$ .............................................. A61B 17/32
[52] U.S. Cl. ...................................... 606/13; 128/398
[58] Field of Search .............................. 606/2, 13–17; 128/395–398

[56] References Cited

U.S. PATENT DOCUMENTS

| | | | |
|---|---|---|---|
| 4,126,136 | 11/1978 | Auth et al. | 128/303.1 |
| 4,233,493 | 11/1980 | Nath | 128/303.1 |
| 4,693,244 | 9/1987 | Daikuzono | 128/398 |
| 4,736,743 | 4/1988 | Daikuzono | 128/303.1 |
| 4,799,479 | 1/1989 | Spears | 128/303.1 |
| 4,832,979 | 5/1989 | Hoshino | 128/303.1 |
| 4,848,339 | 7/1989 | Rink et al. | 128/398 |

FOREIGN PATENT DOCUMENTS

| | | | |
|---|---|---|---|
| 0069351 | 1/1983 | European Pat. Off. | 606/17 |
| 2182565 | 5/1987 | United Kingdom | 606/13 |
| 2185188 | 7/1987 | United Kingdom . | |

OTHER PUBLICATIONS

Suzuki et al., "Endoscopic Local Hyperthermia with Nd-YAG Laser-Experimental Study and Development of Computed Thermo-System" *Bulletin of the Japan Society of Laser Medicine*, vol. 6, No. 3, Jan. 1986, pp. 347–350.

*Primary Examiner*—Max Hindenburg
*Attorney, Agent, or Firm*—Lowe, Price, LeBlanc & Becker

[57] ABSTRACT

A laser light transmitting probe having at least one flat surface, which transmits laser light to living tissue to permit an incision, vaporization, an exfoliation and hemostasis. According to a preferred embodiment, a base portion of the probe is provided with a cylindrical part, a conical part and two flat surfaces formed on the both sides of the conical part. A surface layer, which contains laser light absorbing particles, laser light scattering particles having a larger refractive index than that of the material of the probe and a binder made from a laser light transmissible material, is formed on the flat surface for effective laser light irradiation. Due to the structure of a flat part provided with the flat surfaces, various types of surgical treatments can be performed for various types of treated target are of tissue with only this probe.

7 Claims, 7 Drawing Sheets

Figure 5
Figure 6
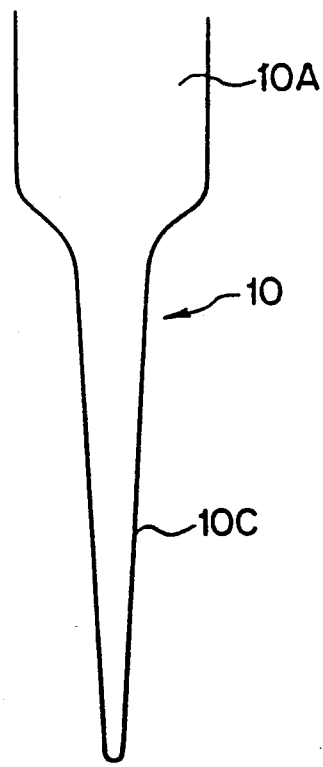
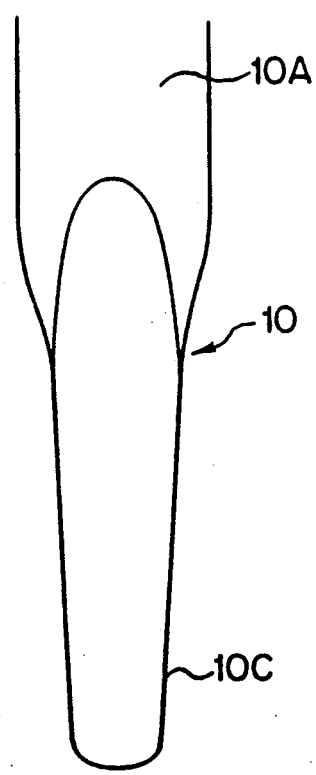

LASER LIGHT TRANSMITTING PROBE

BACKGROUND OF THE INVENTION

This invention relates to a laser light transmitting probe, which transmits laser light to living tissue of an animal such as a human body to permit an incision, vaporization of the living tissue or a thermal therapy.

Medical treatments such as incisions of living tissue of animal organisms by irradiation with laser light have become common due to the ability thereof to concurrently provide hemostasis.

It had been conventional that the laser light was irradiated from the fore end of an optical fiber which is held back out of contact with the living tissue. But this method causes severe damage to the fore end portion of the optical fiber. Therefore, a method which has been utilized lately is as follows; at first, the laser light, after being transmitted into an optical fiber system, is fed into a transmitting probe being brought into contact with or being held out of contact with the living tissue (hereafter "living tissue" is sometimes expressed by "tissue" only). Then the laser light emitted from the surface of the probe is irradiated on the tissue.

The inventor developed many kinds of contact probes which are utilized for various purposes. One embodiment is shown in FIG. 15. This probe 50 is made of sapphire, quartz and the like, and usually, its fore end portion is tapered and conical shaped uniformly.

However, referring to FIG. 15, laser light L is fed by means of an optical fiber 51 into the probe 50, which is of long and narrow conical shape with a round tip end and whose outer surface is smooth. The laser light L passing through the probe 50 is reflected and refracted on an inner surface to reach the tip end, finally is emitted from the tip end.

This conventional probe produces a power density and power distribution of the laser light L as shown as contour lines H and curve Pd, respectively, in FIG. 15. Accordingly, it is obvious that the laser light L is concentratedly emitted from the tip end of the probe 50. Therefore, the effective area of the laser light irradiation is very small and exists only in living tissue adjacent to the inserted portion of the probe.

On the other hand, when medical operations are carried out, various surgical treatments such as an incision, vaporization, an exfoliation of the tissue and occasionally hemostasis for ulcerated tissue are required.

In these prior art procedures, the exfoliation can not be carried out by the laser light irradiation, thus, only mechanical incisions have been applied. Further, when the large target area having ulcerated tissue is exfoliated, a medical cutter must be moved many times little by little.

SUMMARY OF THE INVENTION

It is therefore an object of the present invention to provide a laser light transmitting probe, which permits efficiently for living tissue treatments such as an exfoliation and hemostasis as well as an incision and vaporization.

The present invention features a laser light transmitting probe comprising a base portion to which laser light is applied and a fore end portion of the probe emits the laser light. The fore end portion is provided with at least one flat surface.

In a preferred embodiment, the fore end portion is provided with a conical part and the flat surface is formed on at least one side of the conical part at the fore end thereof.

In another preferred embodiment, the probe is symmetric with respect to its axis.

In still another preferred embodiment, a surface layer containing laser light absorbing particles, laser light scattering particles having a larger refractive index than that of the material of the probe and a binder made from a laser light transmissible material is formed on at least the flat surface. Further, the surface layer is preferably formed on a roughened surface covering at least the flat surface.

Hereafter, the part of the fore end portion of the probe, which is provided with at least one flat surface, is expressed as a flat part.

According to the present invention, the energy power level of the laser light emitted from the tip end of the probe is normally the highest, the next highest power level is that of the light emitted from the side-edges of the flat part, and the lowest power level corresponds to light from the flat surface, although the level changes a little due to the structure of the probe. Therefore, after the laser light is fed into the probe, by emitting the laser light from the tip end, the tissue can be incised efficiently and by emitting from the flat surface, treatments requiring low energy level of laser light such as wooding for ulcerated tissue can be carried out. Then, using the side-edges of the flat part, the exfoliation or so called side-incision can be performed easily. Further, by inserting the tip end or the both side-edges of the flat part into the tissue, a small target area can be treated. Accordingly, as various types of surgical treatments can be performed with only this probe, any other special probes are not required. That is to say, this probe can be used suitably for many kinds of purposes.

By providing the surface layer, with the above mentioned three kinds of particles contained in the surface layer, the effective area of laser light irradiation is enlarged and the vaporization of the tissue is accelerated. Accordingly, the tissue can be incised with a low energy of the laser light. Therefore, when the tissue is incised, the probe can be moved rapidly. As a result, the surgery can be carried in short time, further with a cheap and small scaled laser light generator.

Further objects and advantages of the present invention will be apparent from the following description, reference being had to the accompanying drawing wherein preferred embodiments of the present invention are clearly shown.

BRIEF DESCRIPTION OF THE DRAWINGS

FIG. 5 is a side view of another probe;

FIG. 6 is a front view of still another probe;

DESCRIPTION OF THE PREFERRED EMBODIMENT

Now, the present invention is described more particularly.

Figure 1:
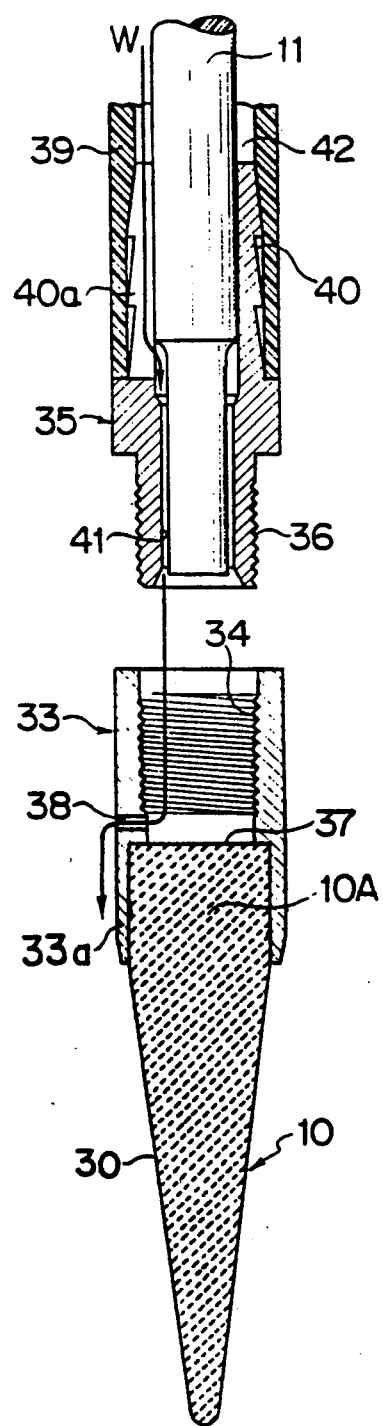
FIG. 1 is a longitudinal sectional view of a probe and a holding member therefor relating to the present invention.
Figures 2, 3, 4:
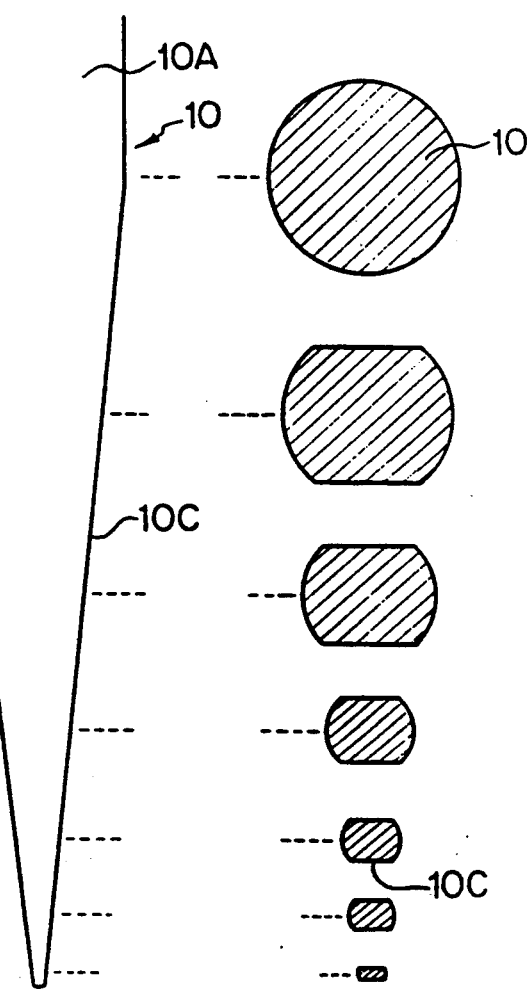
FIG. 2 is a front view of a probe.
FIG. 3 is a side view of the probe.
FIG. 4 shows a series of transverse sectional views of the probe which are shown one by one longitudinally.

As shown in FIGS. 1, 2, 3 and 4, the probe 10 is symmetric with respect to the axis of the probe 10 and consists of a base portion comprising a cylindrical part 10A, a substantial conical part 10B at its lower part and two flat surfaces 10C on the sides of the conical part 10B, in a penetrating direction of laser light. The flat surfaces 10C are formed by partial and longitudinal cutting away of the both sides of the conical part 10B. Although the shape of the tip end of the flat surface 10C might be selected properly, since the conical part 10B is not of an exactly conical shape in this embodiment, as viewed in FIG. 2, it is of a substantially semi-circle shape. As shown in FIG. 4, since the conical part 10B is tapered down to the tip end, it is apparent that the distance between the flat surfaces 10C is gradually shorter approaching the tip end of the flat surface 10C.

As shown in FIGS. 2-4, the resulting probe shape produces a conical fore end portion 10B which tapers to a tip. In the exemplary embodiment shown in these drawings, the fore end portion 10B has a two arcuate lateral side surfaces joined by the flat surfaces 10C. Effectively, the flat surfaces 10C are formed between the pair of arcuate surfaces. The flat surfaces 10C each extend to the tip of the probe 10 to define an edge between the pair of arcuate lateral side surfaces. Also, the flat surfaces 10C taper or become narrow at the tip. The tip curves in the direction between the lateral side surfaces, such that at least the opposite ends of the edge are rounded at the points where the edge joins the arcuate side surfaces. In the embodiment of FIG. 2, the edge is entirely rounded to form an arc between the side surfaces. In contrast, the embodiment of FIG. 5 includes an edge along the tip which is rounded at the points where the edge joins the arcuate side surfaces so as to form rounded corners. As depicted in FIG. 4, the size of the arc of each of the arcuate side surfaces is progressively smaller along the taper of the fore end portion toward the tip shown at the bottom of that drawing.

In a modified embodiment (not shown) a fore end portion is provided with an exact conical part at its lower part, then, flat surfaces are formed on the both sides of the exact conical part.

FIG. 5 shows a side view of the probe having another structure. This probe 10 is symmetric with respect to the axis of the probe 10. Then, in the fore-end portion of the probe 10, a long and narrow conical shaped flat part, which has two flat surfaces 10C on its both sides, is projected from a cylindrical base part 10A. FIG. 6 shows a front view of the probe having still another structure. In the fore end of this probe 10, a flat part, which has at least one flat surface 10C and whose upper part is tapered down for some distance and lower part keeps substantially the same diameter to the end, is projected from a cylindrical base part 10A. Therefore, the upper part of the flat surface 10C is of a substantially part of an elliptical shape and the lower part of the flat surface 10C is of a substantially rectangular shape.

The above mentioned various probes 10 provided with flat surfaces 10C are held by holding members respectively, for example, as shown in FIG. 1.

The cylindrical base part 10A of the probe 10 is fitted in a cylindrical female connector 33 and fixed integrally thereto by caulking the mating portions 33a, by using a ceramic type adhesive between the mating surfaces or by the combination of both of these means. The female connector 33 has, on the internal surface thereof, a female thread 34 which is adapted to mate removably with male threads 36 of a male connector 35. The female connector 33 has holes 38 which facilitate the passage of cooling water W from the inside to the outside thereof. The holes 38 are disposed adjacent to the top of a light receiving base 37 of the probe 10, and for example, oppositely on the circumference of the female connector 33, although only one of them is shown in FIG. 1.

On the other hand, the male connector 35 is pressed to be fitted into an end portion of a flexible tube jacket 39 fabricated of, for example, Teflon (the trademark for polytetrafluoroethylene). For this press fitting, the male connector 35 has stepped portions 40 at its base portion in order to be firmly held by the tube jacket 39 so as not to be removed.

A transmitting optical fiber 11 for the laser light is inserted in the tube jacket 39 and the male connector 35. There is a passage 42 between the optical fiber 11 and the tube jacket 39 for passage of the cooling water W. The transmitting optical fiber 11 is closely fitted in the tube jacket 39 at its stepped portion 40. Then, the stepped portion 40 has, for example, two slits 40a formed oppositely on a circumference of the stepped portion 40 for letting the cooling water W pass therethrough. A gap 41 for the cooling water W is further provided between the inner surface of the end portion of the male connector 35 and the outer surface of the transmitting optical fiber 11.

the probe held by the above mentioned holding member serves as a laser light emitter while the female connector 33 is connected to mate with the male connector 35. In this case, the emitter is equipped in an endoscope and some other suitable holders. As a result, pulse laser light transmitted through the transmitting optical fiber 11 penetrates into the probe 10 from the light receiving base 37 and is emitted from the whole outer surface of the inserting portion 30 of the probe 10. At the same time, the cooling water W is fed through the passage 42, the slit 40a and the gap 41 to cool the probe 10. The water W is discharged through the opening 38 to flow out on the surface of the living tissue to cool it as well.

A surface layer 5, which is formed on the surface of the transmissible member 1 for effective laser light irradiation, will be explained hereinafter. The transmissible member could be any one of the probes 10 illustrated in FIGS. 1 to 4.

Figure 7:
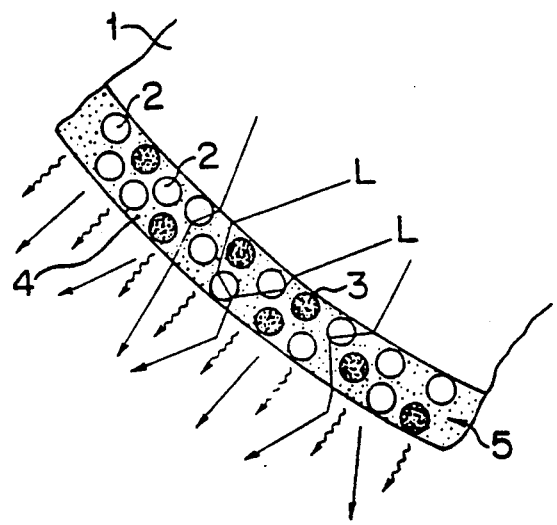
FIGS. 7 and 8 are enlarged sectional views of surface layers covering a transmissible member.

FIG. 7 shows an enlarged sectional view of the surface layer 5 covering the above mentioned probes shown in FIGS. 1, 2, 3 and 4.

As shown in FIG. 7, a transmissible member 1, which consists of the probe, is covered with the surface layer 5 which contains light scattering particles 2 made of sapphire and the like having a larger refractive index than that of the transmissible member 1. While laser light L emitted from the transmissible member 1 passes through the surface layer 5, the laser light L, which impinges on the light scattering particle 2, is partially reflected on the surface of the light scattering particle 2, or partially penetrates into and is emitted from the particle 2 with refraction. Therefore, the laser light L is emitted in various directions from the whole surface layer 5. This produces a large area of laser light irradiation.

Further, the surface layer 5 contains laser light absorbing particles 3 made of carbon and the like. Accordingly, when the laser light L impinges on the laser light absorbing particle 3, the greater part of the energy of the laser light L is converted to heat energy by means of the laser light absorbing particle 3, and the tissue is heated by the heat energy from the surface layer 5 particularly when contacted by the probe.

By so doing, as the vaporization of the tissue is accelerated, the tissue can be incised with a low energy of the laser light penetrated into the transmissible member 1. Therefore, when the tissue is incised, the transmissible member 1 can be moved rapidly. In other words, the probe 10 can be moved rapidly. Further, high power level of the laser light is not required when the laser light is penetrating into the transmissible member 1. As a result, the medical operation can be carried out in short time, with a cheap and small scaled laser light generator.

If the surface layer 5 is produced by coating a dispersion containing the laser light absorbing particles 3 and light scattering particles 2 on the surface of the transmissible member 1, after a vaporization of the dispersion medium, the contact of the probe 10 with the tissue or other substances causes a damage to the surface layer 5 because both kinds of particles 2, 3 are attached to the surface of the transmissible member 1 only by physical adsorptive power.

Therefore, provisions of a binder to attach the laser light absorbing particles 3 and the light scattering particles 2 to the surface of the transmissible member 1 enhances adhesion of the surface layer 5 to the transmissible member 1.

In this case, the binder is preferably made of light transmissible material 4 such as quartz and the like to ensure the emission of the laser light from the surface layer 5. Laser light transmissible particles which have a melting point the same as or lower than that of the transmissible member 1 are preferably used as the transmissible material 4 and are dispersed together with the absorbing particles 3 and the light scattering particles 2 in a proper liquid such as water. Then the transmissible member 1 painted with this dispersion is baked at a temperature which is higher than a melting point of the transmissible particle but within a limit allowing the transmissible member 1 to keep its shape during baking. Accordingly, the transmissible binder particles melt to form the surface layer 5 of high mechanical strength together with the laser light absorbing particles 3 and the light scattering particles 2. Therefore, the damages to the surface layer 5 can be reduced because of its high strength.

Figure 8:
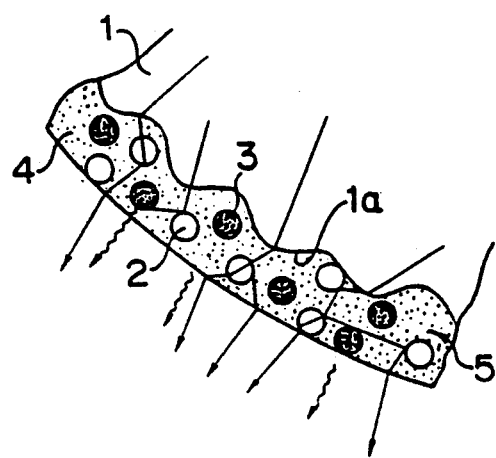

Furher, as shown in FIG. 8, forming a rough surface 1a on the transmissible member 1 under the surface layer 5 increases the scattering effect of the laser light.

The transmissible member 1, which consists of the probe 10 of the present invention, is preferably fabricated from a natural or artifical ceramic material such as diamond, sapphire, quartz and the like due to their heat resistance.

The light scattering particles 2, which have a larger refractive index for the laser light than that of the transmissible member 1, comprise a natural or artifical material such as diamond, sapphire, quartz (a melting point is preferably high), single crystal zirconium oxide ($ZrO_2$), high melting point glass, transmissible and heat resistant synthetic resin, laser light reflective metal, or a particle which is laser light reflective or non-reflective metal particle coated with laser light reflective metal such as gold, aluminum and the like by means of the surface treatment such as gilding.

The transmissible material 4 is preferably made from the transmissible particles, which melt to form a film and more preferably which has heat resistance, such as natural or artifical sapphire, quartz, glass, transmissible and heat resistant synthetic resin and the like. A suitable transmissible material is selected from these materials in consideration of the relation to the transmissible material 4.

The laser light absorbing particles 3 comprises carbon, graphite, iron oxide, manganese dioxide, or any other materials which can absorb the laser light to generate heat energy.

A content of each particle in the surface layer (wt %) and each average particle size are preferably within ranges shown in a following table respectively. More preferable each content and particle size are put in parentheses.

|  | Content (wt %) | Average Particle Size ($\mu$m) |
| --- | --- | --- |
| Light Scattering Particle (A) | 90–1 (70–20) | 0.2–300 (1–50) |
| Transmissible Particle (B) | 10–90 (20–50) | 0.2–500 |
| Absorbing Particle (C) | 90–1 (70–10) | 0.2–500 (1–100) |

The thickness of the surface layer is preferably 10 $\mu$m–5 mm, more preferably 30 $\mu$m–1 mm. The surface layer is formed by following method. If the surface layer can not be formed to be a desired thickness by one step of the following method, the step should be repeated until a desired thickness can be obtained;

First method; the three kinds of particles are dispersed in a dispersion medium. Then, the medium is heated to a temperature which is higher than the melting point of the transmissible particle. Finally, the transmissible member is dipped in the heated dispersion.

Second method; the three kinds of particles are melted to be sprayed to the transmissible member.

Further, other suitable methods for forming the surface layer can be used.

By the above mentioned first method, the dispersion dispersing the three kinds of particles can be painted to the transmissible member. Moreover, this painting method is easy, because what should be done is that only a part, which is desired to be covered with the surface layer, of the transmissible member is dipped in the dispersion and therefrom pulled up. Therefore, this method is practical and rational.

As the dispersion medium, suitable liquid such as water, alcohol or mixture of them can be used. Further sugar or starch is added to increase the viscosity of the dispersion medium.

As described before, according to the present invention, the forming of the surface layer 5 on the surface of the transmissible member 1 extends the effective area of the laser light irradiation. Because the laser light is emitted widely in many directions from the surface layer 5.

On the other hand, the inventor performed an experiment as follows, using a conical shaped probe, although which has no flat surface.

Figure 13:
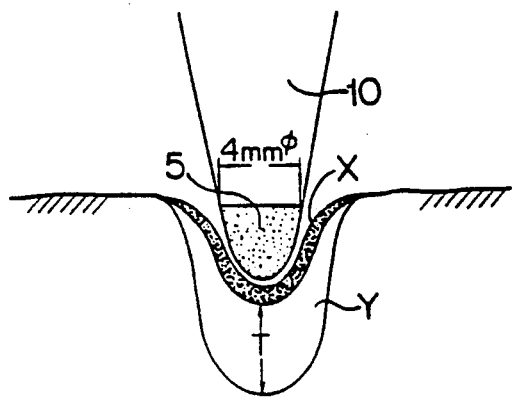
FIG. 13 is a schematic illustration showing a tip end of a probe and power density distribution diagrams of laser light in an experiment.

In the following discussion, the content of the light scattering particle, that of the transmissible particle, and that of the laser light absorbing particle will be referred as (A), (B) and (C) respectively. The inventor investigated each change of following two parameters against (C) under the fixed condition of the ratio of (A):(B)=2:1. One investigated parameter is a laser light power level with which an incision to a pig's liver can be started. Another parameter is the depth T of a coagulation layer Y below a carbonized layer X of treated tissue (T, Y and X are shown in FIG. 13). Then, from the result shown in FIG. 14, the following things are known.

According to the relation of the power level and the percentage of (C), when the percentage of (C) is high, the incision can be started with the low power level of the laser light, then it is possible for the probe to be moved quickly. Then, according to the relation of the depth T and the percentage of (C), as the percentage of (C) is increased, the depth T is decreased. Since the effect of hemostasis can be known by the depth T, the hemostasis of the treated tissue turned out to decrease as the percentage of (C) is increased.

Therefore, the probe with high percentage of (C) in the surface layer can be used effectively for the incision of tissue which is subject to damage to some extent such as skin, fat layer and the like.

On the other hand, the probe with low percentage of (C) can be used efficiently for incision to the tissue, for which the hemostasis is considered important. This type of the tissue is, for example, liver, heart and the like. In this case, it is clear that the laser light power level of the output from a laser light generator must be raised and the probe must be moved slowly.

Referring to this experiment and the like, the inventor introduced these two equations, (1) and (2).

$$\frac{(C)}{(A)+(B)+(C)} \propto \frac{\text{Quantity of laser light for heating}}{\text{Incident laser energy}} \quad (1)$$

$$\frac{(A)+(B)}{(A)+(B)+(C)} \propto \frac{\text{Quantity of laser light for transmitting}}{\text{Incident laser energy}} \quad (2)$$

Equation (1) means that heat generation is progressed as (C) is increased. Accordingly, under high percentage of (C), an incision is carried out by mainly vaporization. Therefore, since most of the incident laser light energy is spent for the heating, the laser light can not penetrate so deeply into the tissue. As a result, the depth of the coagulation layer is reduced.

Equation (2) means that penetration of the laser light into the tissue is progressed as (C) is decreased. Accordingly, under the low percentage of (C), the tissue absorbing laser light is heated, thus, the coagulation is made in the tissue.

Figure 14:
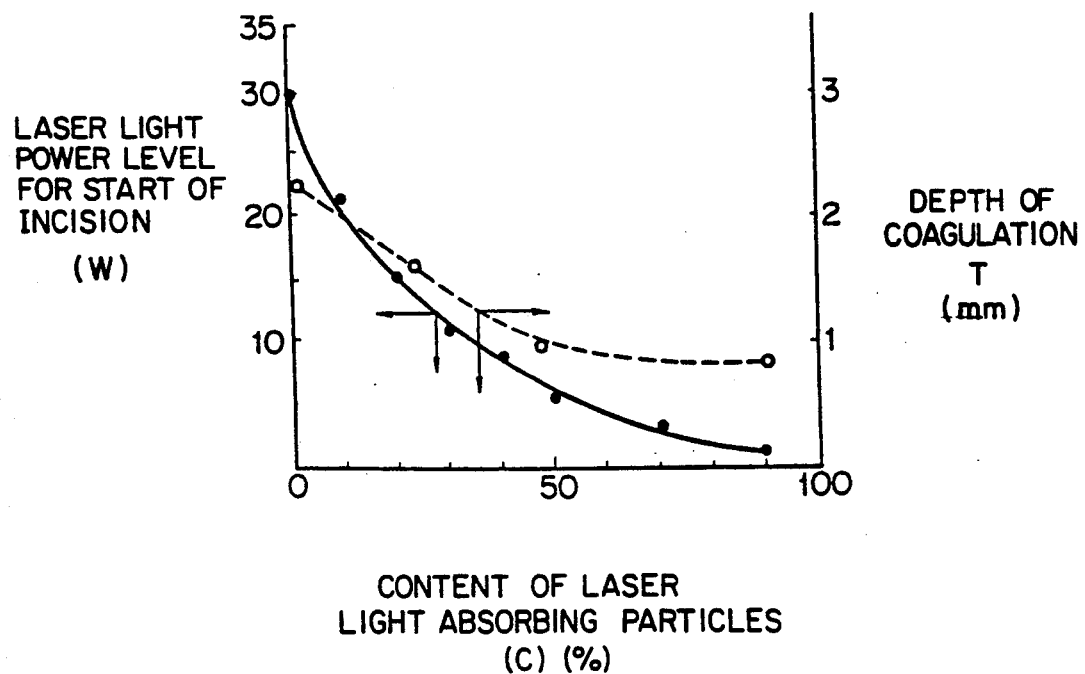
FIG. 14 is a graph showing the result of the experiment in FIG. 13.
Figure 15:
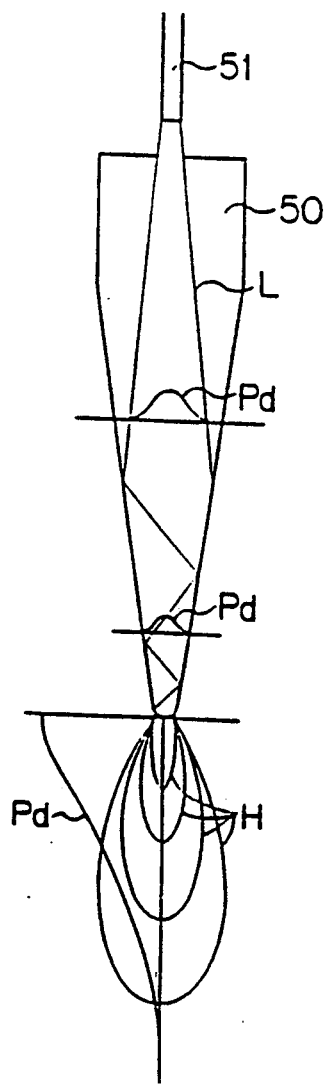
FIG. 15 is a front view of an earlier probe developed by the inventor.

It is needless to say, these results correspond to the result of the above mentioned experiment shown in FIG. 14.

Therefore, if a number of probes which differ only as to the percentage of (C) in the surface layers are prepared in advance, a suitable probe can be selected in accordance with each medical purpose, thereby a suitable treatment can be carried out easily. Further, according to the present invention, since the probe 10 is provided with at least one flat surface, a wider variety of treatments can be carried out.

Figure 9:
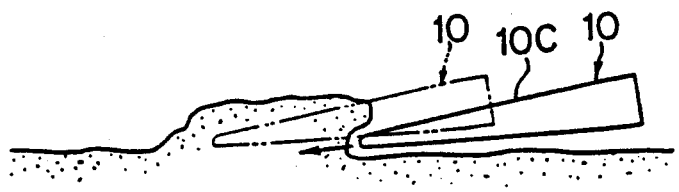
FIG. 9 is a schematic illustration showing operation with a probe for an incision or an exfoliation.

Now, operation of the probe 10 of the present invention will be explained referring to FIGS. 9, 10 and 11.

First the probe 10 of the present invention can incise or exfoliate the tissue. In this case, as shown in FIG. 9, the probe 10 is moved to the left or in a direction indicated by an arrow in this figure and/or is swung in a transverse direction to the moving direction. As another method, the probe 10 can be placed vertically to the surface of the tissue so as to be stood up for incising the tissue.

Figure 10:
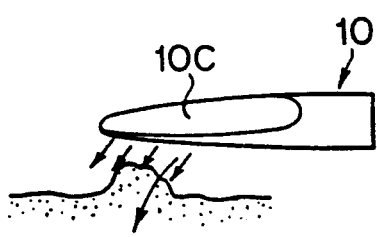
FIG. 10 is a schematic illustration showing operation with the side-edge of a flat part for an incision or an exfoliation.

Second, as shown in FIG. 10, a tumor and the like produced on the tissue can be cut away or exfoliated by the both side-edges of the flat part moved in a direction indicated by arrows in this figure.

Figure 11:
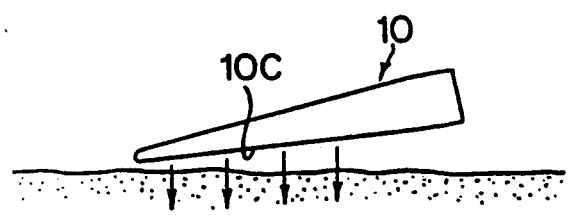
FIG. 11 is a schematic illustration showing operation with a flat surface for hemostasis.

Further, as shown in FIG. 11, hemostasis for an ulcerated part can be carried out by laser light irradiation with small energy from the flat surface 10C facing the ulcerated part.

Figure 12:
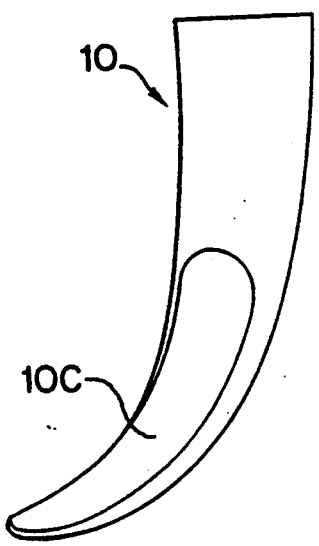
FIG. 12 is a perspective view of another probe.

FIG. 12 shows another embodiment of the probe 10, the fore end portion of a base portion bends or curves at a certain angle on a longitudinal cross section. In this probe 10, at least one flat surface 10C is formed on the bending fore end portion. By this probe 10, another type of effective area of the laser light irradiation can be obtained.

While preferred embodiments have been described, it is apparent that the present invention is not limited to the specific embodiments thereof.

What is claimed is:

1. A laser light transmitting probe comprising:
   a base onto which laser light impinges;
   a body through which said laser light penetrates; and
   a semi-circular conical fore end portion which emits said laser light, wherein:
   (i) said semi-circular conical fore end portion tapers to a tip,
   (ii) said fore end portion has a pair of arcuate side surfaces joined by at least one flat surface formed between said pair of arcuate side surfaces, said at least one flat surface extending to said tip to define an edge between said pair of arcuate side surfaces along said tip, said at least one flat surface narrowing toward the tip, and
   (iii) said tip is rounded at least along portions of said edge adjacent to said pair of arcuate side surfaces such that at least opposite ends of said edge are rounded.

2. A laser light transmitting probe as defined in claim 1, wherein:
   said at least one flat surface comprises first and second flat surfaces formed on opposite sides of the fore end portion each formed between and joining together said pair of arcuate side surfaces such that said probe is symmetric with respect to the axis of said probe, and
   the size of the arc of each of the arcuate surfaces is progressively smaller along the taper of said fore end portion toward said tip.

3. A laser light transmitting probe as defined in claim 1, wherein:

said fore end portion is at least partially bent at a certain angle relative to a longitudinal cross section to form a bent part of the fore end portion, and said at least one flat surface is formed on the bent part of the fore end portion.

4. A laser light transmitting probe as defined in claim 1, further comprising a surface layer containing laser light absorbing particles and laser light scattering particles having a larger refractive index than that of the material of said probe, wherein said surface layer is formed at least on said at least one flat surface.

5. A laser light transmitting probe as defined in claim 4, wherein said surface layer is provided on a rough surface formed at least on said at least one flat surface.

6. A laser light transmitting probe as defined in claim 1, further comprising a surface layer containing laser light absorbing particles, laser light scattering particles having a larger refractive index than that of the material of said probe and a binder made from a laser light transmissible material wherein said surface layer is formed at least on said at least one flat surface.

7. A laser light transmitting probe as defined in claim 6, wherein said surface layer is provided on a rough surface formed at least on said at least one flat surface.

* * * * *